US00PP35607P2

(12) United States Plant Patent
Arts

(10) Patent No.: US PP35,607 P2
(45) Date of Patent: Jan. 30, 2024

(54) ***MANDEVILLA* PLANT NAMED 'MAN222901'**

(50) Latin Name: *Mandevilla sanderi*
Varietal Denomination: MAN222901

(71) Applicant: MBA B.V., De Kwakel (NL)

(72) Inventor: Niels Arts, Aalsmeer (NL)

(73) Assignee: MBA B.V., De Kwakel (NL)

( * ) Notice: Subject to any disclaimer, the term of this patent is extended or adjusted under 35 U.S.C. 154(b) by 0 days.

(21) Appl. No.: 18/199,603

(22) Filed: May 19, 2023

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./226, 232
See application file for complete search history.

*Primary Examiner* — Karen M Redden
(74) *Attorney, Agent, or Firm* — C. Anne Whealy

(57) ABSTRACT

A new and distinct cultivar of *Mandevilla* plant named 'MAN222901', characterized by its upright to spreading and vining plant habit; vigorous growth habit and moderate growth rate; glossy dark green-colored leaves; early and freely flowering habit; and relatively large bright red-colored flowers.

2 Drawing Sheets

Figure 1:
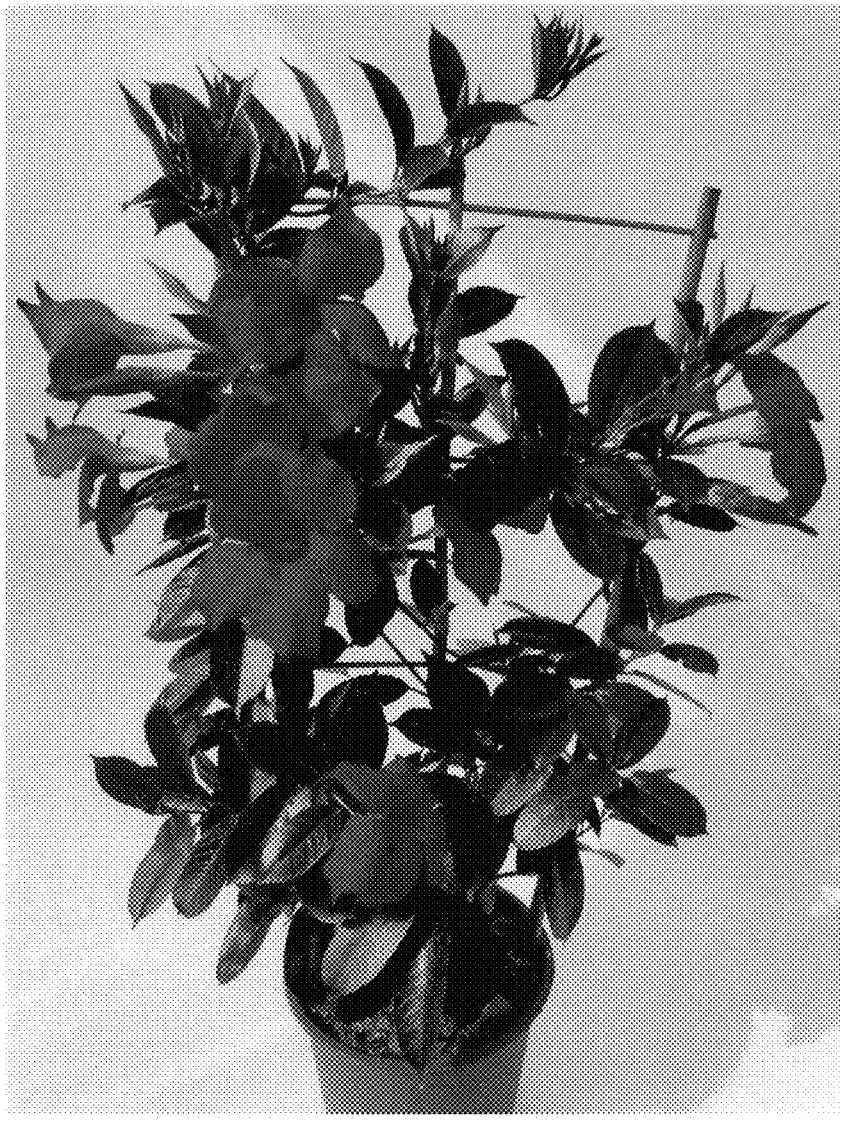

Botanical designation: *Mandevilla sanderi*.
Cultivar denomination: 'MAN222901'.

CROSS-REFERENCED TO CLOSELY-RELATED APPLICATIONS

An European Community Plant Breeder's Rights application for the instant plant was filed by the Applicant/Assignee, MBA B.V. of De Kwakel, The Netherlands, on Apr. 21, 2022, application number 2022/1067. Foreign priority is not claimed to this application.

BACKGROUND OF THE INVENTION

The present invention relates to a new and distinct cultivar of *Mandevilla* plant, botanically known as *Mandevilla sanderi* and hereinafter referred to by the name 'MAN222901'.

The new *Mandevilla* plant is a product of a planned breeding program conducted by the Inventor in De Kwakel, The Netherlands. The objective of the breeding program is to create new freely-flowering *Mandevilla* plants with large attractive flowers and good container performance.

The new *Mandevilla* plant originated from a cross-pollination in De Kwakel, The Netherlands during the summer of 2016 of *Mandevilla sanderi* 'Sunparapibra', disclosed in U.S. Plant Pat. No. 19,649, as the female, or seed parent with a proprietary selection of *Mandevilla sanderi* identified as code number 12-0152-162, not patented, as the male, or pollen, parent. The new *Mandevilla* plant was discovered and selected by the Inventor as a single flowering plant from within the progeny of the stated cross-pollination in a controlled greenhouse environment in De Kwakel, The Netherlands during the summer of 2019.

Asexual reproduction of the new *Mandevilla* plant by vegetative cuttings in a controlled greenhouse environment in De Kwakel, The Netherlands, since the summer of 2019 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'MAN222901'. These characteristics in combination distinguish 'MAN222901' as a new and distinct *Mandevilla* plant:

1. Upright to spreading and vining plant habit.
2. Vigorous growth habit and moderate growth rate.
3. Glossy dark green-colored leaves.
4. Early and freely flowering habit.
5. Relatively large bright red-colored flowers.

Plants of the new *Mandevilla* can be compared to plants of the female parent, 'Sunparapibra'. Plants of the new *Mandevilla* differ primarily from plants of 'Sunparapibra' in flower color as plants of the new *Mandevilla* have bright red-colored flowers whereas plants of 'Sunparapibra' have light pink-colored flowers. In addition, plants of the new *Mandevilla* have larger flowers than plants of 'Sunparapibra'.

Plants of the new *Mandevilla* can be compared to plants of the male parent selection. Plants of the new *Mandevilla* differ primarily from plants of male parent selection in flower color as plants of the new *Mandevilla* have bright red-colored flowers whereas plants of the male parent selection have white-colored flowers.

Plants of the new *Mandevilla* can be compared to plants of *Mandevilla sanderi* 'MAN216902', disclosed in U.S. Plant Pat. No. 29,848. In side-by-side comparisons, plants of the new *Mandevilla* differ primarily from plants 'MAN216902' in the following characteristics:

1. Plants of the new *Mandevilla* are larger than plants of 'MAN216902'.
2. Plants of the new *Mandevilla* have thicker stems than plants of 'MAN216902'.
3. Plants of the new *Mandevilla* have longer leaves than plants of 'MAN216902'.

4. Plants of the new *Mandevilla* flower earlier than plants of 'MAN216902'.
5. Plants of the new *Mandevilla* are more freely flowering than plants of 'MAN216902'.
6. Plants of the new *Mandevilla* have larger flowers than plants of 'MAN216902'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of typical flowering plant of 'MAN222901' grown in a container.

Figure 2:
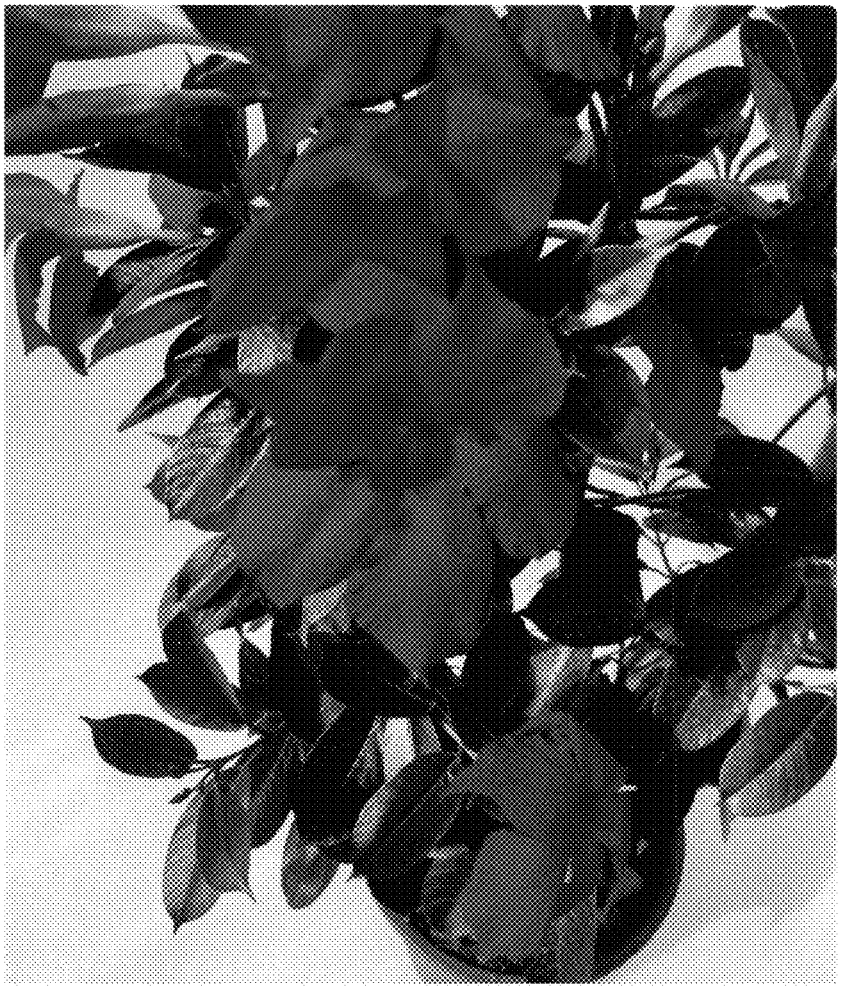

The photograph on the second sheet (FIG. 2) is close-up view of a typical flowering plant of 'MAN222901'.

DETAILED BOTANICAL DESCRIPTION

The aforementioned photographs and following observations, measurements and values describe plants grown during the spring in 19-cm containers in a glass-covered greenhouse in De Kwakel, The Netherlands and under cultural practices typical of *Mandevilla* commercial production. During the production of the plants, day temperatures ranged from 20C to 22C and night temperatures averaged 18C. Plants were pinched one time four weeks after planting and were nine months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'MAN222901'.

Parentage:

*Female, or seed, parent.*—*Mandevilla sanderi* 'Sunparapibra', disclosed in U.S. Plant Pat. No. 19,649.

*Male, or pollen, parent.*—Proprietary selection of *Mandevilla sanderi* identified as code number 12-0152-162, not patented.

Propagation:

*Type.*—By vegetative cuttings.

*Time to initiate roots, summer.*—About 21 days at temperatures about 22C.

*Time to initiate roots, winter.*—About 27 days at temperatures about 22C.

*Time to produce a rooted young plant, summer.*—About 40 days at temperatures about 22C.

*Time to produce a rooted young plant, winter.*—About 50 days at temperatures about 22C.

*Root description.*—Medium in thickness, fibrous to slightly fleshy; typically white to brown in color, actual color of the roots is dependent on substrate composition, water quality, fertilizers, substrate temperature and physiological age of roots.

*Rooting habit.*—Freely branching; medium density.

Plant description:

*Plant and growth habit.*—Upright to spreading and vining plant habit; dense and bushy appearance; vigorous growth habit and moderate growth rate; plants can be produced with or without physical support (trellis).

*Plant height.*—About 55 cm.

*Plant diameter (spread).*—About 35 cm.

*Lateral branch description.*—Branching habit: Moderate branching habit with about two primary branches, each primary branch with about two secondary lateral branches; pinching enhances lateral branch development. Length, primary branches: About 10 cm to 15 cm. Diameter, primary branches: About 5 mm. Internode length: About 2 cm. Strength: Firm. Aspect: Variable, if not on a trellis, erect to about 45 degrees from vertical; plants vining. Texture and luster: Smooth, glabrous; semi-glossy becoming woody and matte with development. Color, developing: Close to 144B. Color, developed: Close to 144A; when woody, close to N199B.

Leaf description:

*Arrangement.*—Opposite, simple.

*Length, fully expanded leaves.*—About 6 cm to 11 cm.

*Width, fully expanded leaves.*—About 3 cm to 4 cm.

*Shape.*—Ovate.

*Apex.*—Cuspidate.

*Base.*—Obtuse.

*Margin.*—Entire.

*Texture and luster, upper and lower surfaces.*—Smooth, glabrous; leathery; glossy.

*Venation pattern.*—Pinnate.

*Color.*—Developing leaves, upper surface: Close to NN137B. Developing leaves, lower surface: Close to 146B. Full expanded leaves, upper surface: Close to NN137A; venation, close to 144A. Fully expanded leaves, lower surface: Close to 147B; venation, close to 144B.

*Petioles.*—Length: About 1 cm to 2 cm. Diameter: About 3 mm to 4 mm. Strength: Strong. Texture and luster, upper and lower surfaces: Smooth, glabrous; glossy. Color, upper and lower surfaces: Close to 144A.

Flower description:

*Flower type and flowering habit.*—Single salverform flowers arranged in axillary racemes; flowers star-shaped and face upright to mostly outwardly; freely flowering habit with about six to ten flowers per inflorescence and during the flowering season, about 40 flowers per plant at one time.

*Natural flowering season.*—Plants flower continuously from the late spring until the late summer in The Netherlands; early flowering habit, plants begin flowering about seven months after planting.

*Flower longevity on the plant.*—About eight to ten days; flowers not persistent.

*Fragrance.*—None detected.

*Inflorescence height.*—About 10 cm.

*Inflorescence diameter.*—About 15 cm.

*Flower buds.*—Length: About 8 cm. Diameter: About 1.5 cm. Shape: Elongated, spindle-shaped. Texture and luster: Smooth, glabrous; semi-glossy. Color: Distally, close to 53A and proximally, close to N144D.

*Flowers.*—Appearance: Flared trumpet, corolla fused and five-parted. Diameter: Relatively large, about 10 cm to 12 cm. Length: About 4 cm to 6 cm. Throat diameter: About 1.5 cm to 2 cm. Tube length: About 3 cm. Tube diameter: About 1.5 cm to 2 cm.

*Corolla.*—Quantity and arrangement: Five petals arranged in a single whorl; proximal portion of the petals are fused into a tube; distal free portions slightly imbricate. Petal length: About 5 cm to 6 cm. Petal width: About 3.5 cm to 4 cm. Petal shape and appearance: Ovate to triangular, asymmetrical. Petal apex: Acute to cuspidate. Petal margin: Entire; slightly undulate. Petal texture and luster, upper and lower surfaces: Smooth, glabrous; semi-glossy. Throat and tube texture: Smooth, glabrous; semi-glossy. Color: Petals, when opening and fully opened, upper surface: Close to N45A; venation, close to N45A; color does not change with subsequent development. Petal, when opening and fully opened, lower surface: Close to N45B; venation, close to N45A; color does not change with subsequent development. Throat: Close to N25A; venation, close to N25A. Tube: Close to N144D; venation, close to N144D.

*Calyx.*—Quantity and arrangement: Five sepals arranged in a single whorl; calyx, star-shaped. Length: About 1 cm. Diameter: About 5 mm. Sepal length: About 1 cm. Sepal width: About 3 mm. Sepal shape: Subulate. Sepal apex: Acute. Sepal margin: Entire. Sepal texture and luster, upper and lower surfaces: Smooth, glabrous; semi-glossy. Sepal color: When opening, upper and lower surfaces: Close to 145A. Fully opened, upper and lower surfaces: Close to 145A.

*Peduncles.*—Length: About 3 cm to 4 cm. Diameter: About 2 mm to 3 mm. Strength: Strong. Aspect: Mostly upright. Texture and luster: Smooth, glabrous; glossy. Color: Close to 144A.

*Pedicels.*—Length: About 1 cm to 2 cm. Diameter: About 3 mm. Strength: Strong. Aspect: Upright to about 30 degrees from peduncle axis. Texture and luster: Smooth, glabrous; glossy. Color: Close to 144B.

*Reproductive organs.*—Stamens: Quantity and arrangement: Typically five; basifixed; anthers connate. Filament color: Close to 14D. Anther size: About 4 mm by 10 mm. Anther shape: Elongate. Anther color: Close to 14D. Pollen amount: Moderate. Pollen color: Close to 14D. Pistils: Quantity: Typically one. Pistil length: About 1 cm to 1.5 cm. Style color: Close to 150B. Stigma diameter: About 2 mm. Stigma shape: Club-shaped. Stigma color: Close to 150D. Ovary color: Close to 150B.

*Fruits and seeds.*—To date, fruit and seed development have not been observed on plants of the new *Mandevilla.*

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 1C to about 45C.

It is claimed:

1. A new and distinct *Mandevilla* plant named 'MAN222901' as illustrated and described.

* * * * *